(12) United States Patent
Chih-Chung

(10) Patent No.: US 7,351,060 B2
(45) Date of Patent: Apr. 1, 2008

(54) ABUTMENT FOR DENTAL IMPLANT

(76) Inventor: Ho Chih-Chung, No. 6-2, Xinxing St., Meinong Town, Kaohsiung County (TW)

( * ) Notice: Subject to any disclaimer, the term of this patent is extended or adjusted under 35 U.S.C. 154(b) by 0 days.

(21) Appl. No.: 11/153,903

(22) Filed: Jun. 14, 2005

(65) Prior Publication Data
US 2006/0281049 A1  Dec. 14, 2006

(51) Int. Cl.
*A61C 8/00* (2006.01)
(52) U.S. Cl. .................................................... 433/173
(58) Field of Classification Search ......... 433/172–176
See application file for complete search history.

(56) References Cited

U.S. PATENT DOCUMENTS

| | | | | |
|---|---|---|---|---|
| 5,906,489 A | * | 5/1999 | Khazzam et al. | 433/176 |
| 5,975,903 A | * | 11/1999 | Shoher et al. | 433/173 |
| 5,989,030 A | * | 11/1999 | Suga | 433/176 |
| 6,302,693 B1 | * | 10/2001 | Mena | 433/172 |
| 6,722,879 B2 | * | 4/2004 | Lin | 433/18 |
| 6,749,430 B2 | * | 6/2004 | Arturo | 433/173 |
| 6,758,672 B2 | * | 7/2004 | Porter et al. | 433/173 |
| 2001/0005577 A1 | * | 6/2001 | Devincenzo | 433/173 |
| 2002/0127515 A1 | * | 9/2002 | Gittleman | 433/172 |
| 2003/0232308 A1 | * | 12/2003 | Simmons, Jr. | 433/173 |
| 2004/0166460 A1 | * | 8/2004 | Devincenzo | 433/18 |

\* cited by examiner

*Primary Examiner*—Cary E. O'Connor
(74) *Attorney, Agent, or Firm*—Townsend and Townsend and Crew LLP

(57) ABSTRACT

The invention relates to an abutment for dental implant. The abutment of the invention comprises: a post portion, a central portion, a head portion and at least one first portion. The post portion extends along a longitudinal axis. The central portion is formed on the post portion, and has a middle section and a peripheral section. The head portion is formed on the middle section of the central portion, and extends upwardly along the longitudinal axis. The first portion is formed on the peripheral section of the central portion, and extends upwardly along at least one first direction with a first angle corresponding to the longitudinal axis. According to the invention, the abutment can provide greater metal support and interlocking engagement for a posterior crown.

5 Claims, 5 Drawing Sheets

ABUTMENT FOR DENTAL IMPLANT

BACKGROUND OF THE INVENTION

1. Field of the Invention

The present invention relates to an abutment, more particularly, an abutment for dental implant that adopts the locking taper or other non-screw connection.

2. Description of the Related Art

The locking taper or non-screwed connection has the character of non-limited direction for connection. Therefore the crown mold on the abutment before connection to the implant is practicable for the clinical practice. One example is the integrated abutment crown (IAC) of Bicon. Bicon owns a dental implant system that adopts the locking taper connection, which is highly respected by many dentists. The IAC is actually an achievement of Bicon. By directly fusing the polyceramic material to the abutment, the IAC is simple and convenient for the dentists to use, and the patients recognize the superiority of polyceramic material. The polyceramic material has elasticity. By offering more space for the polyceramic material, the IAC could exhibit the elasticity to extreme extent. And the elasticity is the most wanted in dental implantology. But Bicon's abutment for the IAC is not without drawbacks. It doesn't provide enough metal support and interlocking engagement for the polyceramic material, which may lead to fracture of IAC.

Referring to FIG. 1, the conventional integrated abutment crown 10 comprises an abutment 11 and a crown 12. The abutment 11 comprises a post portion 111, a central portion 112 and a head portion 113. The post portion 111 is in part used for being connected to the implant. The central portion 112 is formed on the post portion 111. The head portion 113 is formed on the central portion 112. The abutment 11 shown in FIG. 1 is basically a type of conventional abutment that is to be connected to the implant, and later an impression will be taken and finally the crown (or prosthesis) will be cemented onto it. However, as mentioned above, because the head portion 113 is formed as a tapered shape with a tapered angle more than six degrees, the conventional integrated abutment crown 10 can't provide enough metal support and interlocking for the polyceramic material, which may lead to fracture of the conventional integrated abutment crown 10.

Therefore, it is necessary to provide an abutment so as to solve the above problem.

SUMMARY OF THE INVENTION

One objective of the present invention is to provide an abutment for dental implant. The abutment of the invention comprises: a post portion, a central portion, a head portion and at least one first portion. The post portion extends along a longitudinal axis. The central portion is formed on the post portion, and has a middle section and a peripheral section. The head portion is formed on the middle section of the central portion, and extends upwardly along the longitudinal axis. The first portion is formed on the peripheral section of the central portion, and extends upwardly along at least one first direction with a first angle corresponding to the longitudinal axis.

According to the invention, because the first portion extends upwardly along the first direction with the first angle corresponding to the longitudinal axis, the abutment can provide greater metal support for a posterior crown. The first angle can be adjusted according to the shape of the posterior crown. Furthermore, the first portion comprises at least one hole penetrating the first portion so as to provide greater interlocking engagement with the posterior crown.

Another objective of the present invention is to provide an abutment for dental implant. The abutment of the invention comprises: a post portion, a central portion and a head portion. The post portion extends along a longitudinal axis. The central portion is formed on the post portion. The head portion is formed on the central portion, and has at least one hole penetrating the head portion.

According to the invention, the head portion comprises at least one hole penetrating the head portion so as to provide greater interlocking engagement with the anterior crown. Furthermore, the head portion is formed as a non-tapered shape or formed as a tapered shape with a tapered angle less than six degrees, thus the abutment can provide greater metal support for an anterior crown.

DETAILED DESCRIPTION OF THE INVENTION

Figure 1:
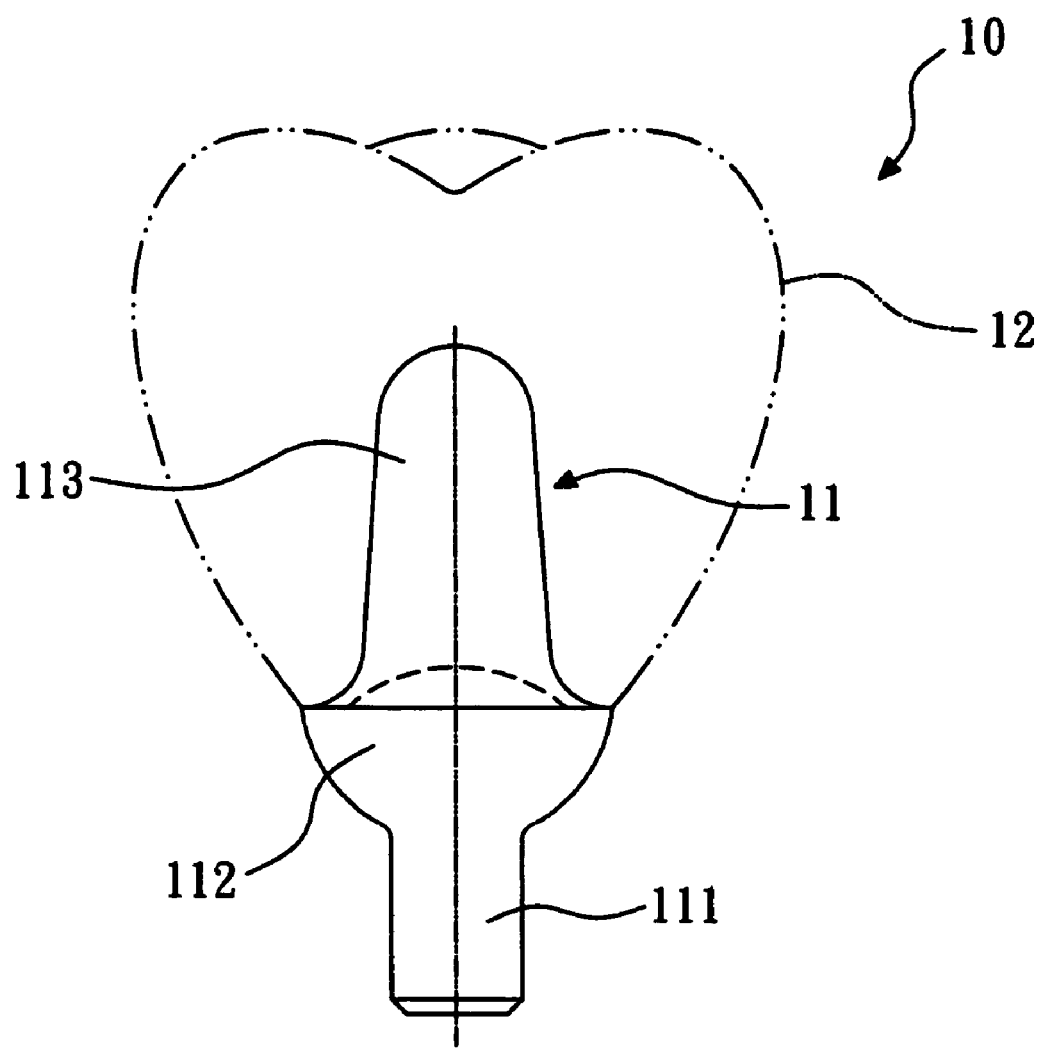
FIG. 1 shows a front view of the conventional integrated abutment crown having a posterior crown indicated in dashed lines.
Figure 2A:
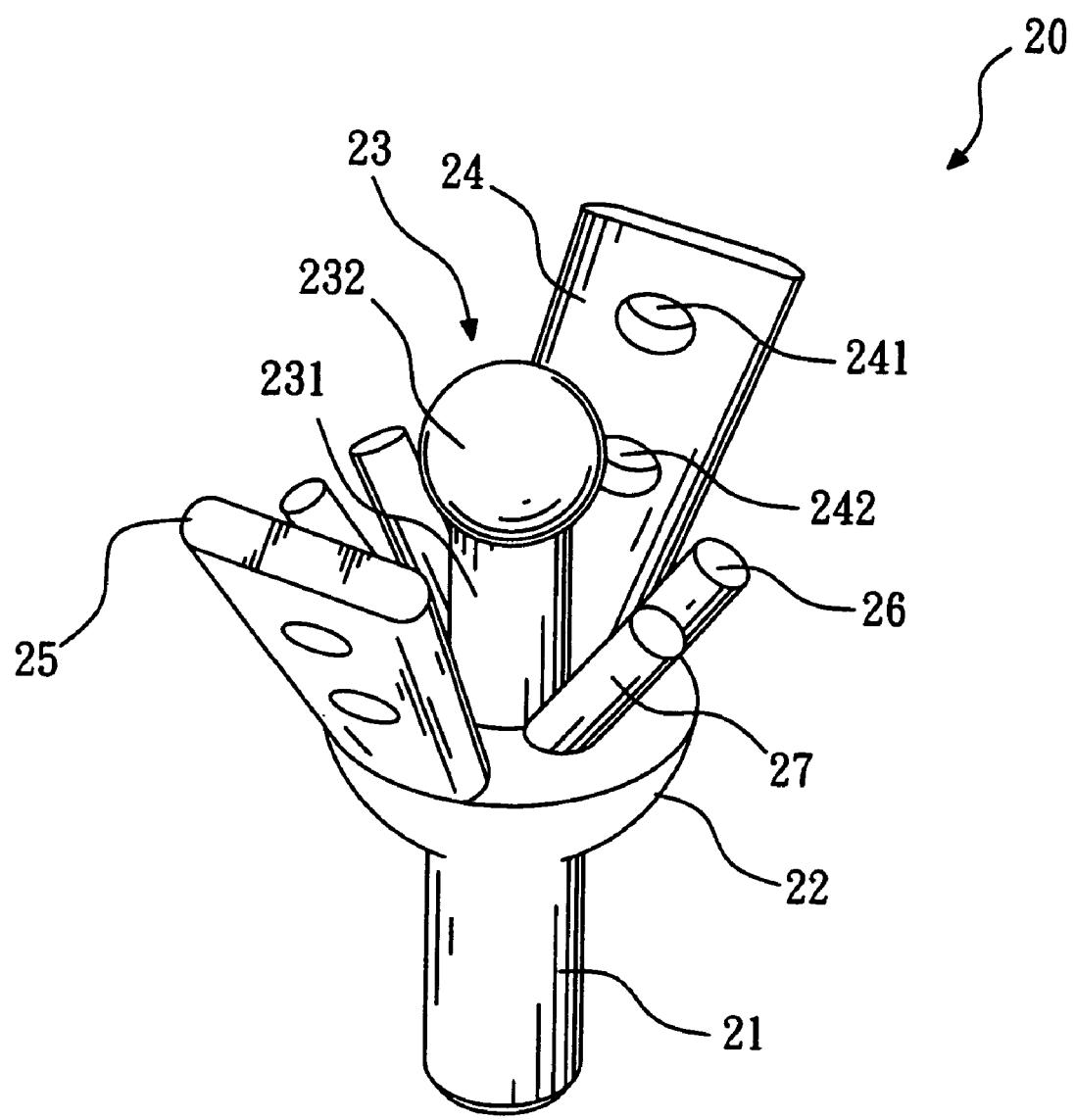
FIG. 2A shows a perspective view of the abutment, according to a first embodiment of the invention.
Figure 2B:
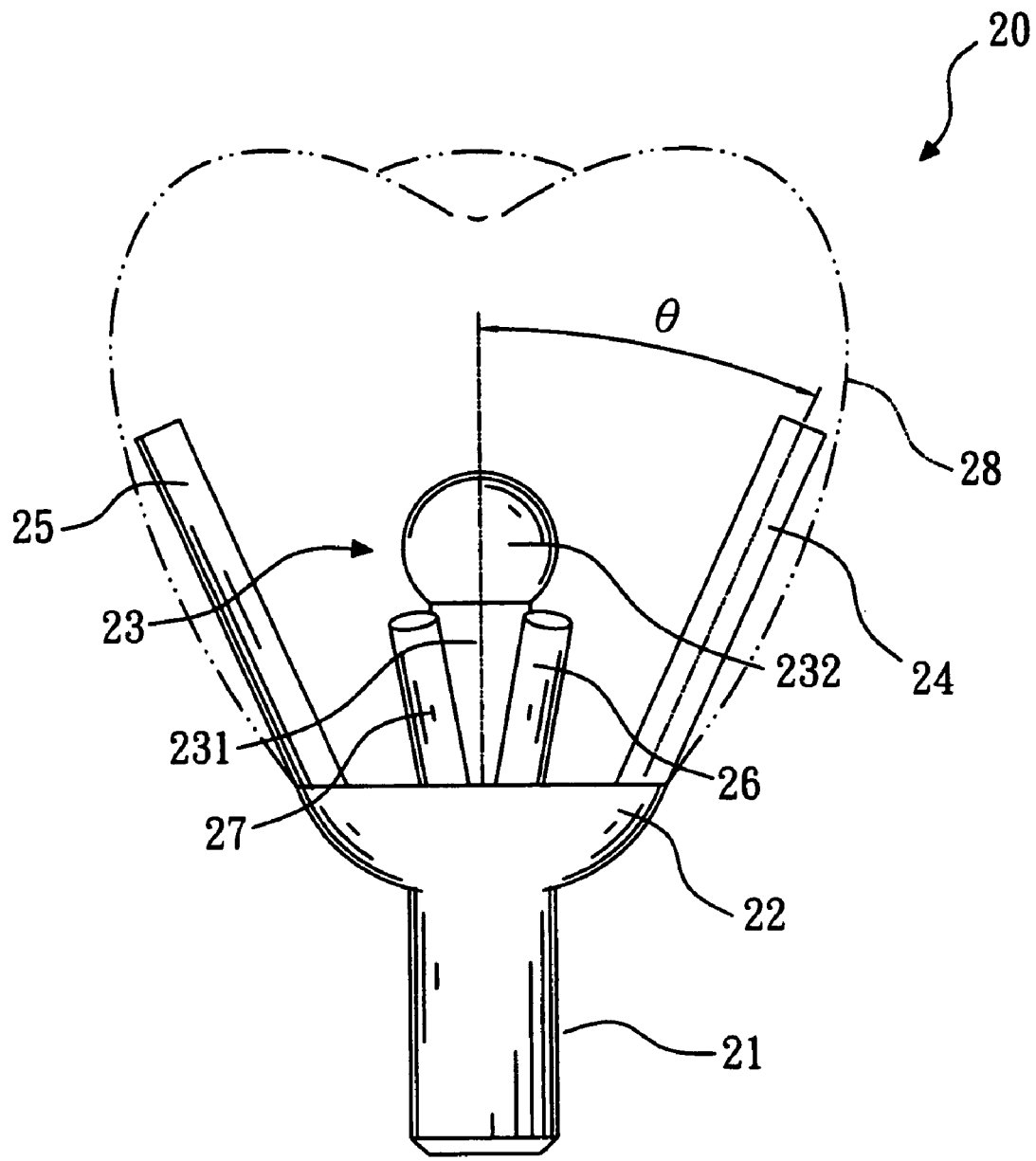
FIG. 2B shows a front view of the abutment with a posterior crown indicated in dashed lines, according to the first embodiment of the invention.

Referring to FIGS. 2A and 2B, according to a first embodiment of the invention, an abutment 20 comprises: a post portion 21, a central portion 22, a head portion 23 and at least one first portion 24, 25. The post portion 21 extends along a longitudinal axis. The central portion 22 is formed on the post portion 21, and has a middle section and a peripheral section. The head portion 23 is formed on the middle section of the central portion 22, and extends upwardly along the same longitudinal axis. The head portion 23 comprises a post section 231 and a round head 232; the round head 232 is formed on the post section 231.

The first portions 24 and 25 are formed on the peripheral section of the central portion 22, and extend upwardly along at least one first direction with a first angle θ corresponding to the longitudinal axis, as shown in FIG. 2B. In other words, the first portion 24 extends from the peripheral section of the central portion 22 outward. The first angle θ can be adjusted according to the shape of the posterior crown 28 (directly integrate crown). Therefore, the abutment 20 can provide greater metal support and interlocking engagement for the posterior crown 28 (directly integrate crown). The material of the posterior crown 28 (directly integrate crown) may be polyceramic, resin, glassionomer or other materials.

The first portion 24 is taken as an example for illustration. The first portion 24 is a plate-like structure with a first length, and comprises two holes 241 and 242 penetrating mesio-distally the first portion 24. When the posterior crown 28 (directly integrate crown) is molded on the abutment 20, there is greater metal support and interlocking engagement between the abutment 20 and the posterior crown 28 (directly integrate crown).

The abutment 20 further comprises at least one second portion 26, 27 formed on the peripheral section of the central portion 22 and extending upwardly along at least one second direction with a second angle corresponding to the longitudinal axis. The second portion 26 is a rod-like structure with a second length. The first length of the first portion is usually longer than the second length of the second portion. The second portion can provide the other side metal support for the posterior crown 28 (directly integrate crown).

Figure 3A:
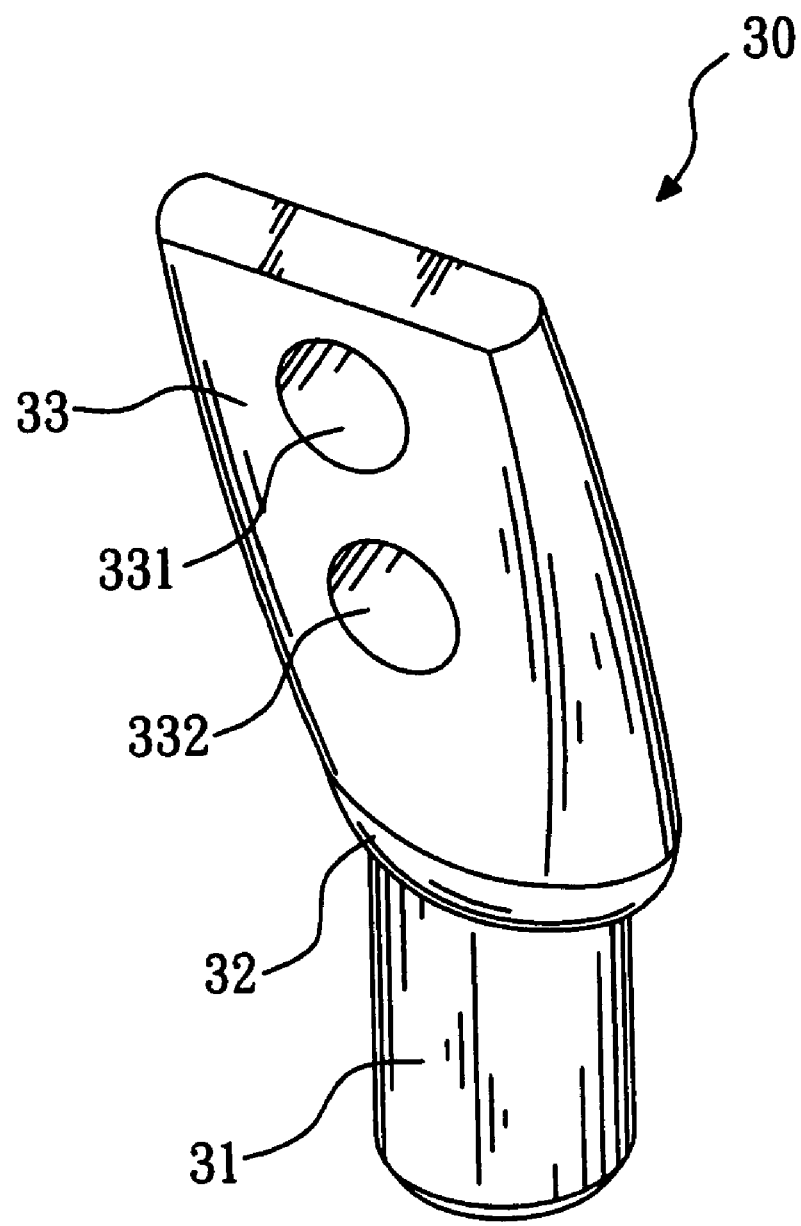
FIG. 3A shows a perspective view of the abutment, according to a second embodiment of the invention.
Figure 3B:
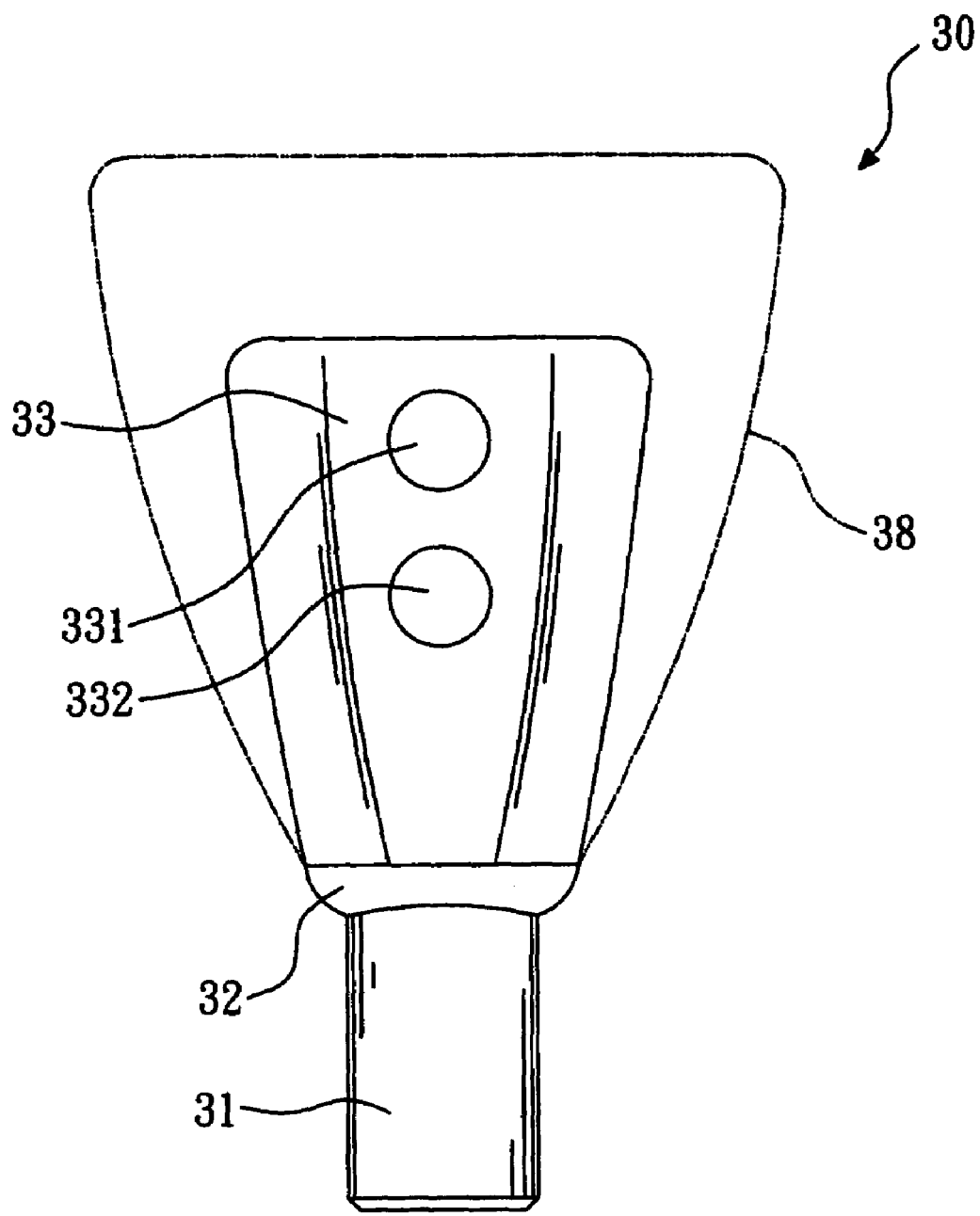
FIG. 3B shows a front view of the abutment with an anterior crown indicated in dashed lines, according to the second embodiment of the invention.

Referring to FIGS. 3A and 3B, according to a second embodiment of the invention, an abutment 30 of the invention comprises: a post portion 31, a central portion 32 and a head portion 33. The post portion 31 extends along a longitudinal axis. The central portion 32 is formed on the post portion 31. The head portion 33 is formed on the central portion 32, and formed as a non-tapered shape. That is, the width of an upper section of the head portion 33 is equal to or larger than that of a bottom section of the head portion 33. Therefore, the abutment 30 can provide greater metal support for the anterior crown 38 so as to prevent the broken anterior crown. Besides, the head portion 33 may be formed as a tapered shape with a tapered angle less than six degrees.

The head portion 33 extends along a first direction with a first angle corresponding to the longitudinal axis. The first angle can be adjusted according to the shape of an anterior crown 38. The head portion 33 is a plate-like structure which comprises two holes 331 and 332 penetrating buccal-lingually. When the anterior crown 38 is molded on the abutment 30, there is greater interlocking engagement between the abutment 30 and the anterior crown 38.

While an embodiment of the present invention has been illustrated and described, various modifications and improvements can be made by those skilled in the art. The embodiment of the present invention is therefore described in an illustrative, but not restrictive, sense. It is intended that the present invention may not be limited to the particular forms as illustrated, and that all modifications which maintain the spirit and scope of the present invention are within the scope as defined in the appended claims.

What claimed is:

1. A non-screw abutment for dental implant, comprising:
   a post portion, extending along a longitudinal axis;
   a central portion, formed on the post portion and having a middle section and a peripheral section;
   a head portion, formed on the middle section of the central portion and extending upwardly along the longitudinal axis; and
   at least one first portion, formed on the peripheral section of the central portion and extending upwardly along at least one first direction with a first angle corresponding to the longitudinal axis.

2. The abutment according to claim 1, wherein the first portion is a plate structure.

3. The abutment according to claim 2, wherein the first portion comprises at least one hole penetrating the plate structure.

4. The abutment according to claim 1, further comprising at least one second portion, formed on the peripheral section of the central portion and extending upwardly along at least one second direction with a second angle corresponding to the longitudinal axis.

5. The abutment according to claim 4, wherein the second portion is a rod structure.

* * * * *